United States Patent
Zhou

(10) Patent No.: US 9,434,777 B2
(45) Date of Patent: *Sep. 6, 2016

(54) NEUREGULIN PEPTIDES AND THEIR USE

(71) Applicant: Zensun (Shanghai) Science & Technology Limited, Shanghai (CN)

(72) Inventor: Mingdong Zhou, Shanghai (CN)

(73) Assignee: Zensun (Shanghai) Science & Technology, Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/657,899

(22) Filed: Mar. 13, 2015

(65) Prior Publication Data

US 2016/0009774 A1    Jan. 14, 2016

Related U.S. Application Data

(63) Continuation of application No. 14/101,084, filed on Dec. 9, 2013, now Pat. No. 9,012,400, which is a continuation of application No. 13/131,682, filed as application No. PCT/CN2009/001236 on Nov. 9, 2009, now Pat. No. 8,609,620.

(60) Provisional application No. 61/118,566, filed on Nov. 28, 2008.

(51) Int. Cl.
*A61K 38/00* (2006.01)
*A61K 38/16* (2006.01)
*C07K 14/00* (2006.01)
*C07K 14/475* (2006.01)
*A61K 38/18* (2006.01)

(52) U.S. Cl.
CPC .......... *C07K 14/4756* (2013.01); *A61K 38/00* (2013.01); *A61K 38/16* (2013.01); *A61K 38/1883* (2013.01); *C07K 14/00* (2013.01)

(58) Field of Classification Search
CPC .. A61K 38/00; A61K 38/16; A61K 38/1883; C07K 14/00; C07K 14/4756
USPC .................. 514/8.3, 16.4, 21.3; 530/324
See application file for complete search history.

(56) References Cited

U.S. PATENT DOCUMENTS

| | | |
|---|---|---|
| 7,063,961 B2 | 6/2006 | Ballinger et al. |
| 7,115,554 B1 | 10/2006 | Sklar et al. |
| 7,226,907 B1 | 6/2007 | Zhou |
| 7,612,164 B2 | 11/2009 | Zhou |
| 7,662,772 B2 | 2/2010 | Marchionni et al. |
| 7,795,212 B2 | 9/2010 | Zhou |
| 7,964,555 B2 | 6/2011 | Zhou |
| 2006/0019888 A1 | 1/2006 | Zhou |
| 2006/0154333 A1* | 7/2006 | Pienkos ............ A61K 38/1808 435/69.1 |
| 2006/0194734 A1 | 8/2006 | Zhou |
| 2006/0199767 A1 | 9/2006 | Zhou |
| 2007/0129296 A1 | 6/2007 | Zhou |
| 2007/0190127 A1 | 8/2007 | Zhou |
| 2007/0213264 A1 | 9/2007 | Zhou |
| 2008/0057064 A1 | 3/2008 | Zhou |
| 2008/0260713 A1 | 10/2008 | Zhou |
| 2009/0156488 A1 | 6/2009 | Zhou |
| 2009/0203595 A1 | 8/2009 | Zhou |
| 2011/0085976 A1 | 4/2011 | Yan et al. |

FOREIGN PATENT DOCUMENTS

| | | |
|---|---|---|
| WO | WO 94/26298 A1 | 11/1994 |
| WO | WO 00/37095 A1 | 6/2000 |
| WO | WO 00/64400 A1 | 11/2000 |
| WO | WO 01/89568 A1 | 11/2001 |
| WO | WO 02/48191 A2 | 6/2002 |
| WO | WO 00/78347 A1 | 12/2002 |
| WO | WO 03/014159 A1 | 2/2003 |
| WO | WO 03/080835 A1 | 10/2003 |
| WO | WO 03/099300 A1 | 12/2003 |
| WO | WO 03/099320 A1 | 12/2003 |
| WO | WO 03/099321 A1 | 12/2003 |
| WO | WO 2007/062594 A1 | 6/2007 |
| WO | WO 2007/076701 A1 | 7/2007 |
| WO | WO 2008/028405 A1 | 3/2008 |
| WO | WO 2009/033373 A1 | 3/2009 |
| WO | WO 2010/060266 A1 | 11/2009 |
| WO | WO 2010/030317 A2 | 3/2010 |

OTHER PUBLICATIONS

Water from http://www.biology-online.org/dictionary/Water, pp. 1-3. Accessed Apr. 24, 2014.*
U.S. Appl. No. 09/979,809, filed Mar. 5, 2002, Zhou.
U.S. Appl. No. 12/207,173, filed Sep. 9, 2008, Zhou.
International Search Report dated Feb. 11, 2010, from International Application No. PCT/CN2009/001236.
Jones et al., "Binding Specificites and Affinities of EGF Domains for ERBB Receptors," FEBS Letters, 447:227-231 (1999).
Qi et al., "Establishment of an ERBB3 and ERBB4-Specific Ligand Screening System, and a Screen of Neuregulin-1 Mutants," Yi Chuan., 32(12):1247-1255 (2010), abstract only.
Xu et al., "Neuregulin-1/ErbB signaling: a druggable target for treating heart failure," Curr. Opin. Pharmacol., 9(2):214-19 (2009).
Corfas et al., "Neuregulin 1-erbB signaling and the molecular/cellular basis of schizophrenia," Nat. Neurosci., 7(6):575-580 (2004).

* cited by examiner

*Primary Examiner* — Julie Ha
(74) *Attorney, Agent, or Firm* — Jones Day

(57) ABSTRACT

Neuregulin peptides useful, for example, in methods and compositions comprising preventing, treating or delaying various diseases or disorders are described.

13 Claims, 1 Drawing Sheet

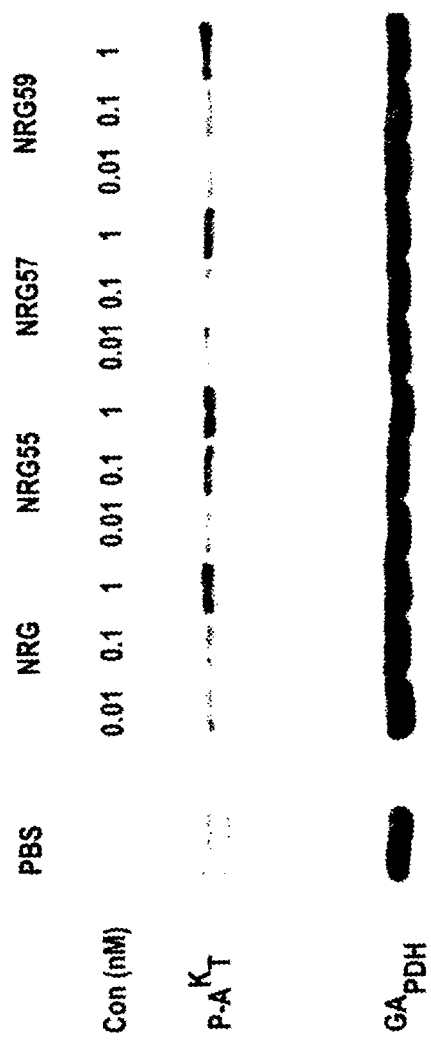

NEUREGULIN PEPTIDES AND THEIR USE

This application is a continuation of application Ser. No. 14/101,084, filed Dec. 9, 2013, now U.S. Pat. No. 9,012,400, which is a continuation of application Ser. No. 13/131,682, filed May 27, 2011, now U.S. Pat. No. 8,609,620, which is a 371 national stage application of PCT/CN2009/001236, having an international filing date of Nov. 9, 2009, which claims the benefit of priority of U.S. provisional application ser. No. 61/118,566, filed Nov. 28, 2008, the entire contents of each of which are incorporated herein by reference.

1. FIELD OF THE INVENTION

This invention relates generally to neuregulin peptides with an enhanced affinity for the ErbB2 receptor and their use for treating various cardiac diseases or disorders.

2. BACKGROUND OF THE INVENTION

Cardiac (ventricular) hypertrophy is an important adaptive physiological response to increased stress or demands for cardiac work. One of the early cellular changes that occurs after a stimulus for hypertrophy is the synthesis of mitochondria and expansion of myofibrillar mass (wall thickening) with a proportional increase in the size of individual cells, but no (or minimal) increase in the number of cells.

When the ventricle is stressed, the initial response is an increase in sarcomere length. This is followed by an increase in the total muscle mass. When the overload is severe; myocardial contractility becomes depressed. In its mildest form, this depression is manifested by a reduction in the velocity of shortening of unloaded myocardium or by a reduction in the rate of force development during isometric contraction. As myocardial contractility becomes further depressed, a more extensive reduction in the velocity of shortening of unloaded myocardium occurs, now accompanied by a decline in isometric force development and shortening. At this point, circulatory compensation may still be provided by cardiac dilation and an increase in muscle mass, which tend to maintain wall stress at normal levels. As contractility falls further, overt congestive heart failure, reflected in a depression of cardiac output and work and/or an elevation of ventricular end-diastolic volume and pressure at rest, supervenes.

The transition from hypertrophy to heart failure is characterized by several alterations in cellular organization. For example, normal hypertrophic cells have a large size with increased and well organized contractile units, as well as strong cell-cell adhesions. In contrast, pathologically hypertrophic cells, which also have large size and accumulation of proteins, display disorganization of contractile proteins (disarray of sarcomeric structures) and poor cell-cell adhesions (disarray of myofibers). Thus, in pathological hypertrophy, the increased size and accumulation of contractile proteins are associated with disorganized assembly of sarcomeric structures and a lack of robust cell-cell interactions.

Heart failure affects approximately five million Americans, and more than 550,000 new patients are diagnosed with the condition each year. Current drug therapy for heart failure is primarily directed to angiotensin-converting enzyme (ACE) inhibitors, which are vasodilators that cause blood vessels to expand, lowering blood pressure and reducing the heart's workload. While the percent reduction in mortality has been significant, the actual reduction in mortality with ACE inhibitors has averaged only 3%-4%, and there are several potential side effects.

ACE inhibitors have also been administered in combination with other drugs such as digitalis, which increases the force of the heart's contractions, and/or a diuretic, which helps relieve the heart's workload by causing the kidneys to remove more sodium and water from the bloodstream. However, at least one study demonstrated no difference in survival associated with the use of digitalis compared with placebo in patients with Class II-III heart failure. Additionally, diuretics can improve some symptoms of heart failure but it is not suitable as a sole treatment.

Additional limitations are associated with other options for preventing or treating heart failure. For example, heart transplantation is clearly more expensive and invasive than drug treatment, and it is further limited by the availability of donor hearts. Use of mechanical devices, such as biventricular pacemakers, are similarly invasive and expensive. Thus, there has been a need for new therapies given the deficiencies in current therapies.

One promising new therapy involves administration of neuregulin (hereinafter referred to as "NRG") to a patient suffering from or at risk of developing heart failure. NRGs comprise a family of structurally related growth and differentiation factors that include NRG1, NRG2, NRG3 and NRG4 and isoforms thereof. For example, over 15 distinct isoforms of NRG1 have been identified and divided into two large groups, known as α- and β-types, on the basis of differences in the sequence of their essential epidermal growth factor (EGF)-like domains. NRG-1 is described, for example, in U.S. Pat. Nos. 5,530,109, 5,716,930, and 7,037,888; Lemke, *Mol. Cell. Neurosci.*1996, 7:247-262; Peles and Yarden, 1993, *Bio Essays* 15:815-824, 1993; Peles et al., 1992, *Cell* 69, 205-216; Wen et al., 1992, *Cell* 69, 559-572, 1992, Holmes et al., 1992, *Science* 256:1205-1210, Falls et al., 1993, *Cell* 72:801-815, Marchionni et al. 1993, *Nature* 362:312-8, the contents of which are incorporated by reference in their entireties. NRG-2 is described, for example, in Chang et al., 1997, *Nature* 387:509-512; Carraway et al., 1997, *Nature* 387:512-516; Higashiyama et al., 1997, *J. Biochem.* 122:675-680, Busfield et al., 1997, *Mol. Cell. Biol.* 17:4007-4014 and International Pat. Pub. No. WO 97/09425), the contents of which are incorporated by reference in their entireties. NRG-3 is described, for example, in Hijazi et al., 1998, *Int. J Oncol.* 13:1061-1067, the contents of which are incorporated by reference in their entireties. NRG-4 is described, for example, in Harari et al., 1999 *Oncogene.* 18:2681-89, the contents of which are incorporated by reference in their entireties.

NRGs bind to the EGF receptor family, which comprises EGFR, ErbB2, ErbB3 and ErbB4, each of which plays an important role in multiple cellular functions, including cell growth, differentiation and survival. They are protein tyrosine kinase receptors, consisting of an extracellular ligand-binding domain, transmembrane domain and cytoplasmic tyrosine kinase domain. After NRG binds to the extracellular domain of ErbB3 or ErbB4, it induces a conformational change that leads to heterodimer formation between ErbB3, ErbB4 and ErbB2 or homodimer formation between ErbB4 itself, which results in phosphorylation of the receptors' C-terminal domain inside the cell membrane. The phosphorylated intracellular domain then binds additional signal proteins inside the cell, activating the corresponding downstream AKT or ERK signaling pathway, and inducing a series of cell reactions, such as stimulation or depression of cell proliferation, cell differentiation, cell apoptosis, cell migration or cell adhesion. Among these receptors, mainly ErbB2 and ErbB4 are expressed in the heart.

It has been shown that the EGF-like domains of NRG1, ranging in size from 50 to 64-amino acids, are sufficient to bind to and activate these receptors. Previous studies have shown that neuregulin-1β (NRG-1β)can bind directly to ErbB3 and ErbB4 with high affinity. The orphan receptor, ErbB2, can form heterodimer with ErbB3 or ErbB4 with higher affinity than ErbB3 or ErbB4 homodimers. Research in neural development has indicated that the formation of the sympathetic nervous system requires an intact NRG-1β, ErbB2 and ErbB3 signaling system. Targeted disruption of the NRG-1β or ErbB2 or ErbB4 led to embryonic lethality due to cardiac development defects. Recent studies also highlighted the roles of NRG-1β, ErbB2 and ErbB4 in the cardiovascular development as well as in the maintenance of adult normal heart function. NRG-1β has been shown to enhance sarcomere organization in adult cardiomyocytes. The short-term administration of a recombinant NRG-1β EGF-like domain significantly improves or protects against deterioration in myocardial performance in three distinct animal models of heart failure. More importantly, NRG-1β significantly prolongs survival of heart failure animals. These effects make NRG-1β promising as a broad spectrum therapeutic or lead compound for heart failure due to a variety of common diseases. However, there remains a need for more effective NRG peptides that can be used in a clinical setting for the prevention, treatment or delaying of heart failure and/or cardiac hypertrophy.

3. SUMMARY OF THE INVENTION

The present invention provides neuregulin peptides having an enhanced affinity for an ErbB receptor. In some embodiments, the neuregulin peptides of the invention comprise an EGF domain of neuregulin. In some embodiments, the neuregulin peptides of the invention comprise an EGF domain of human neuregulin β2 isoform. In some embodiments, the neuregulin peptides having an enhanced affinity for an ErbB receptor comprise the amino acid sequence of SEQ ID NO:5.

The neuregulin peptides of the invention have an enhanced affinity for an ErbB receptor compared to the affinity of the wild type full length neuregulin. In addition to ErbB receptor binding, The neuregulin peptides can possess one or more other biological activities of a native heregulin.

The neuregulin peptides can be prepared according to any technique apparent to those of skill. Exemplary techniques for the preparation of the neuregulin peptides are described herein. In some embodiments, the neuregulin peptides can be prepared recombinantly. In certain embodiments, the neuregulin peptides can be prepared synthetically, for example by solution phase or solid phase peptide synthesis.

The present invention also provides nucleic acid-molecules, vectors and host cells related to the neuregulin peptides of the invention. A nucleic acid molecule of the invention encodes, or is complementary to a nucleic acid molecule encoding, a neuregulin peptide of the invention or a fragment thereof. The nucleic acid molecule can be double- or single-stranded DNA or RNA. A nucleic acid molecule of the invention can be inserted into an appropriate vector for propagation and/or expression of an encoded neuregulin peptide. Such vectors are introduced into suitable hosts, for example, to allow recombinant production of a neuregulin peptide.

The neuregulin peptides of the invention are useful in a variety of therapeutic and non-therapeutic applications. In particular, neuregulin peptides can be used in treating receptor for preventing, treating or delaying various cardiac diseases or disorders. Accordingly, the invention encompasses a pharmaceutical composition comprising a neuregulin peptide and related treatment methods.

In another aspect, the invention provides methods for treating heart failure in a mammal. In certain embodiments, the method comprise the step of administering the neuregulin peptides of the invention into a mammal in need thereof.

In another aspect, the invention provides method s for inducing the phosphorylation of ErbB receptors in a cell. In certain embodiments, the method comprise the step of contacting the cell with the neuregulin peptides of the invention.

In another aspect, the invention provides method s for inducing or sustaining activation of the ERK signaling pathway in a cardiac cell. In certain embodiments, the method comprise the step of contacting the cardiac cell with the neuregulin peptides of the invention.

In another aspect, the invention provides method s for inducing or sustaining activation of the ERK signaling pathway in a cardiac cell. In certain embodiments, the method comprise the step of contacting the cardiac cell with the neuregulin peptides of the invention.

4. BRIEF DESCRIPTION OF THE DRAWING

FIG. 1 shows the effect of NRG55, NRG57 and NRG59 at different concentration on the phosphorylation of AKT in cardiomyocytes. GAPDH was showed to compare the amount of protein in each sample.

5. DETAILED DESCRIPTION OF THE INVENTION 5.1 Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a", "an", and "the" mean "at least one" or "one or more" unless the context clearly dictates otherwise.

As used herein, "epidermal growth factor-like domain" or "EGF-like domain" refers to a peptide motif encoded by the neuregulin gene that binds to and activates ErbB2, ErbB3, ErbB4, or combinations thereof, and bears a structural similarity to the EGF receptor-binding domain as disclosed in WO 00/64400, Holmes et al., Science, 256:1205-1210 (1992); U.S. Pat. Nos. 5,530,109 and 5,716,930; Hijazi et al., Int. J. Oncol., 13:1061-1067 (1998); Chang et al., Nature, 387:509-512 (1997); Carraway et al., Nature, 387: 512-516 (1997); Higashiyama et al., J. Biochem., 122:675-680 (1997); and WO 97/09425, the contents of which are all incorporated herein by reference. In certain embodiments, EGF-like domain binds to and activates ErbB2/ErbB4 or ErbB2/ErbB3 heterodimers. In certain embodiments, EGF-like domain comprises the amino acid sequence of the receptor binding domain of NRG-1. In some embodiments, EGF-like domain comprises the amino acid sequence corresponding to amino acid residues 177-226, 177-237, or 177-240 of NRG-1. In certain embodiments, EGF-like domain comprises the amino acid sequence of the receptor binding domain of NRG-2. In certain embodiments, EGF-like domain comprises the amino acid sequence of the receptor binding domain of NRG-3. In certain embodiments, EGF-like domain comprises the amino acid sequence of the receptor binding domain of NRG-4. In certain embodiments, EGF-like domain comprises the amino acid sequence of Ala Glu Lys Glu Lys Thr Phe Cys Val Asn Gly Gly Glu Cys Phe Met Val Lys Asp Leu Ser Asn Pro (SEQ ID NO:11), as described in U.S. Pat. No. 5,834,229.

As used herein, an "effective amount" of an active agent for treating a particular disease is an amount that is sufficient to ameliorate, or in some manner reduce the symptoms associated with the disease. The amount may cure the disease but, typically, is administered in order to ameliorate the symptoms of the disease.

As used herein, "active agent" means any substance intended for the diagnosis, cure, mitigation, treatment, or prevention of disease in humans and other animals, or to otherwise enhance physical and mental well being.

As used herein, "amelioration" of the symptoms of a particular disorder by administration of a particular active agent refers to any lessening, whether permanent or temporary, lasting or transient that can be attributed to or associated with administration of the agent.

As used herein, "treat", "treatment" and "treating" refer to any manner in which the symptoms of a condition, disorder or disease are ameliorated or otherwise beneficially altered. The effect may be prophylactic in terms of completely or partially preventing a disease or symptom thereof and/or may be therapeutic in terms of a partial or complete cure for a disease and/or adverse effect attributable to the disease. Treatment also encompasses any pharmaceutical use of the compositions herein.

As used herein, "vector (or plasmid)" refers to discrete elements that are used to introduce heterologous DNA into cells for either expression or replication thereof. Selection and use of such vehicles are well known within the skill of the artisan. An expression vector includes vectors capable of expressing DNA that are operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, "cardiac muscle cell differentiation" means a condition characterized by the decrease in DNA synthesis by more than 10%, inhibition of other factor-stimulated DNA synthesis more than 10%, well organized sarcomeric structures and cell-cell adhesions, sustained activation of MAP kinases, and enhanced expression of $p21^{CIP1}$. Further discussion is provided in WO00/37095, the contents of which are incorporated herein by reference in their entireties.

As used herein, "ejection fraction" or "EF" means the portion of blood that is pumped out of a filled ventricle as the result of a heartbeat. It may be defined by the following formula: (LV diastolic volume—LV systolic volume)/LV diastolic volume.

As used herein, "fractional shortening" or "FS" means a ratio of the change in the diameter of the left ventricle between the contracted and relaxed states. It may be defined by the following formula: (LV end diastolic diameter —LV end systolic diameter)/LV end diastolic diameter.

As used herein, "heart failure" means an abnormality of cardiac function where the heart does not pump blood at the rate needed for the requirements of metabolizing tissues. Heart failure includes a wide range of disease states such as congestive heart failure, myocardial infarction, tachyarrhythmia, familial hypertrophic cardiomyopathy, ischemic heart disease, idiopathic dilated cardiomyopathy, myocarditis and the like. The heart failure can be caused by any number of factors, including, without limitation, ischemic, congenital, rheumatic, or idiopathic forms. Chronic cardiac hypertrophy is a significantly diseased state which is a precursor to congestive heart failure and cardiac arrest.

As used herein, "myocardial infarction" refers to a blockade of a coronary artery or blood flow interruption leading to focal necrosis of part of the myocardium caused by severe and persistent ischemia.

As used herein, "organized, or enhanced organization of sarcomeres or sarcomeric structures" means a condition characterized by the straight array of contractile proteins revealed by immunofluorescent staining of α-actinin in cardiac muscle cells. The straight array of α-actinin proteins in cells can be distinguished by microscopy and its connected photography. As used herein, "disorganized or disarray of sarcomeres or sarcomeric structures" means the opposite of the "organized, or enhanced organization of sarcomeres or sarcomeric structures"

As used herein, "organized, or enhanced organization of cytoskeleton structures" means a condition characterized by the straight actin fibers revealed by phalloidin staining of cardiac muscle cells. The straight actin fibers in cells can be distinguished by microscopy and its connected photography as exampled in figures of this specification. As used herein, "disorganized or disarray of cytoskeleton structures" means the opposite of "organized, or enhanced organization of cytoskeleton structures".

As used herein, "protein" is synonymous with "peptide" or "peptide" unless the context clearly dictates otherwise.

As used herein, "sustained activation of MAP kinases" means that the phosphorylated state of MAP kinases, p42/44, is maintained for at least 21 hr in cells. Further discussion is provided in WO00/37095, the contents of which are incorporated herein by reference.

The terms "synergistic, "synergistic effect" and like are used herein to describe improved treatment effects obtained by combining one or more therapeutic agents with one or more retinoic acid compounds. Although a synergistic effect in some fields is meant an effect which is more than additive (e.g., 1+1=3), in the field of medical therapy an additive (1+1=2) or less than additive (1+1=1.6) effect may be synergistic. For example, if each of two drugs were to inhibit the development of ventricular muscle cell hypertrophy by 50% if given individually, it would not be expected that the two drugs would be combined to completely stop the development of ventricular muscle cell hypertrophy. In many instances, due to unacceptable side effects, the two drugs cannot be administered together. In other instances, the drugs counteract each other and slow the development of ventricular muscle cell hypertrophy by less than 50% when administered together. Thus, a synergistic effect is said to be obtained if the two drugs slow the development of ventricular muscle cell hypertrophy by more than 50% while not causing an unacceptable increase in adverse side effects.

As used herein "cardiac hypertrophy" means a condition characterized by an increase in the size of individual ventricular muscle cells, the increase in cell size being sufficient to result in a clinical diagnosis of the patient or sufficient as to allow the cells to be determined as larger (e.g., 2-fold or more larger than non-hypertrophic cells). It may be accompanied by accumulation of contractile proteins within the individual cardiac cells and activation of embryonic gene expression.

In vitro and in vivo methods for determining the presence of ventricular muscle cell hypertrophy are known. In vitro assays for ventricular muscle cell hypertrophy include those methods described WO00/37095, e.g., increased cell size and increased expression of atrial natriuretic factor (ANP). Changes in cell size are used in a scoring system to determine the extent of hypertrophy. These changes can be viewed with an inverted phase microscope, and the degree of hypertrophy scored with an arbitrary scale of 7 to 0, with 7 being fully hypertrophied cells, and 3 being non-stimulated cells. The 3 and 7 states may be seen in Simpson et al. (1982) Circulation Res. 51: 787-801, FIGS. 2, A and B, respectively. The correlation between hypertrophy score and cell surface area (μm2) has been determined to be linear (correlation coefficient=0.99). In phenylephrine-induced hypertrophy, non-exposed (normal) cells have a hypertrophy score of 3 and a surface area/cell of 581 μm2 and fully hypertrophied cells have a hypertrophy score of 7 and a surface area/cell of 1811 μm2, or approximately 200% of normal. Cells with a hypertrophy score of 4 have a surface area/cell of 771 μm2, or approximately 30% greater size than non-exposed cells; cells with a hypertrophy score of 5 have a surface area/cell of 1109 μm2, or approximately 90% greater size than non-exposed cells; and cells with a hypertrophy score of 6 have a surface area/cell of 1366 μm2, or approximately 135% greater size than non-exposed cells. The presence of ventricular muscle cell hypertrophy preferably includes cells exhibiting an increased size of about 15% (hypertrophy score 3.5) or more. Inducers of hypertrophy vary in their ability to induce a maximal hypertrophic response as scored by the above-described assay. For example, the maximal increase in cell size induced by endothelin is approximately a hypertrophy score of 5.

As used herein, "suppression of cardiac hypertrophy" means a reduction in one of the parameters indicating hypertrophy relative to the hypertrophic condition, or a prevention of an increase in one of the parameters indicating hypertrophy relative to the normal condition. For example, suppression of ventricular muscle cell hypertrophy can be measured as a reduction in cell size relative to the hypertrophic condition. Suppression of ventricular muscle cell hypertrophy means a decrease of cell size of 10% or greater relative to that observed in the hypertrophic condition. More preferably, suppression of hypertrophy means a decrease in cell size of 30% or greater; most preferably, suppression of hypertrophy means a decrease of cell size of 50% or more. Relative to the hypertrophy score assay when phenylephrine is used as the inducing agent, these decreases would correlate with hypertrophy scores of about 6.5 or less, 5.0-5.5, and 4.0-5.0, respectively. When a different agent is used as the inducing agent, suppression is examined relative to the maximum cell size (or hypertrophic score) measured in the presence of that inducer.

Prevention of ventricular muscle cell hypertrophy is determined by preventing an increase in cell size relative to normal cells, in the presence of a concentration of inducer sufficient to fully induce hypertrophy. For example, prevention of hypertrophy means a cell size increase less than 200% greater than non-induced cells in the presence of maximally stimulating concentration of inducer. More preferably, prevention of hypertrophy means a cell size increase less than 135% greater than noninduced cells; and most preferably, prevention of hypertrophy means a cell size increase less than 90% greater than non-induced cells. Relative to the hypertrophy score assay when phenylephrine is used as the inducing agent, prevention of hypertrophy in the presence of a maximally-stimulating concentration of phenylephrine means a hypertrophic score of about 6.0-6.5, 5.0-5.5, and 4.0-4.5, respectively.

In vivo determination of hypertrophy may include measurement of cardiovascular parameters such as blood pressure, heart rate, systemic vascular resistance, contractility, force of heartbeat, concentric or dilated hypertrophy, left ventricular systolic pressure, left ventricular mean pressure, left ventricular end-diastolic pressure, cardiac output, stroke index, histological parameters, and ventricular size and wall thickness. Animal models available for determination of development and suppression of ventricular muscle cell hypertrophy in vivo include the pressure-overload mouse model, RV murine dysfunctional model, transgenic mouse model, and post-myocardial infarction rat model. Medical methods for assessing the presence, development, and suppression of ventricular muscle cell hypertrophy in human patients are known, and include, for example, measurements of diastolic and systolic parameters, estimates of ventricular mass and pulmonary vein flows.

Hypertrophy may be from any cause which is responsive to retinoic acid, including congenital viral, idiopathic, cardiotrophic, or myotrophic causes, or as a result of ischemia or ischemic insults such as myocardial infarction. Typically, the treatment is performed to stop or slow the progression of hypertrophy, especially after heart damage, such as from ischemia, has occurred. Preferably, for treatment of myocardial infarctions, the agent(s) is given immediately after the myocardial infarction, to prevent or lessen hypertrophy.

As used herein, "activity unit" or "1U" means the quantity of standard product that can induce 50% maximal reaction. In other words, to determine the activity unit for a given active agent, the EC50 must be measured. For example, if the EC50 for a batch of product was 0.067 μg/ml then that would be one unit. Further, if 1 μg of that product is being used then 14.93 U (1/0.067) is being used. The EC50 can be determined by any method known in the art, including the method employed by the inventors in the Examples below. This determination of the activity unit is important for quality control of genetically engineered products and clinically used drugs, permits product from different pharmaceuticals and/or different batch numbers to be quantified with uniform criteria.

In certain embodiments, unit of neuregulin is determined by measuring the activity of neuregulin through kinase receptor activation enzyme-linked immunosorbant assay (KIRA-ELISA) as described in detail in WO03/099300, and Sadick et al., 1996, Analytical Biochemistry, 235:207-14, the contents of which are incorporated by reference in their entireties. Briefly, the assay measures neuregulin induced ErbB2 activation and phosphorylation on the adherent breast carcinoma cell line, MCF-7. Membrane proteins are solubilized via Triton X-100 lysis and the receptor is captured in ELISA wells coated with ErbB2-specific antibodies (e.g., H4) with no cross-reaction to ErbB3 or ErbB4. The degree of receptor phosphorylation is then quantified by antiphosphotyrosine ELISA.

5.2 Neuregulin Peptides of the Invention

The present invention provides neuregulin peptides capable of binding an ErbB receptor. In some embodiments, neuregulin peptides have an enhanced affinity for an ErbB receptor. In some embodiments, the neuregulin peptides of the invention comprise an EGF domain of neuregulin. In some embodiments, the neuregulin peptides of the invention comprise an EGF domain of human neuregulin β2 isoform. In some embodiments, the neuregulin peptides comprise the amino acid sequence selected from SEQ ID NOs:3, 5, 7 and 9.

In some embodiments, the neuregulin peptides comprise the amino acid sequence of SEQ ID NO: 3. In preferred embodiments, the neuregulin peptide consists of the amino acid sequence of SEQ ID NO:3.

In some embodiments, the neuregulin peptides comprise the amino acid sequence of SEQ ID NO: 5. In preferred embodiments, the neuregulin peptide consists of the amino acid sequence of SEQ ID NO:5.

In some embodiments, the neuregulin peptides comprise the amino acid sequence of SEQ ID NO: 7. In preferred embodiments, the neuregulin peptide consists of the amino acid sequence of SEQ ID NO:7.

The neuregulin peptides of the invention have an enhanced affinity for an ErbB receptor compared to the affinity of the wild type full length neuregulin. In addition to ErbB receptor binding, The neuregulin peptides can possess one or more other biological activities of a native heregulin.

5.2.1 Preparation of the Neuregulin Peptides

The neuregulin peptides can be prepared according to any technique apparent to those of skill. Exemplary techniques for the preparation of neuregulin are described, for example, in U.S. Pat. Nos. 7,226,907, 5,367,060, WO 94/026298, WO 03/099300, the contents of which are hereby incorporated by reference in its entirety.

The neuregulin peptides of the invention can be prepared according to any technique apparent to those of skill. In certain embodiments, the neuregulin peptides of the invention can be prepared synthetically, for example by solution phase or solid phase peptide synthesis. See Merrifield, 1963, *J. Am. Chem. Soc.* 85:2149; Fields et al., 1990, *Int J Pept Protein Res.* 35:161-214; Fields et al., 1991, *Pept Res.* 4:95-101; the contents of which are hereby incorporated by reference in their entirety.

In further embodiments, the neuregulin peptides can be obtained from natural sources, recombinant sources or commercial sources. In some embodiments, the neuregulin peptides can be obtained by recombinantly expressing and then purifying the neuregulin peptides.

The neuregulin peptides can be purified by any art-known technique such as high performance liquid chromatography, ion exchange chromatography, gel electrophoresis, affinity chromatography and the like. The actual conditions used to purify a particular neuregulin will be apparent to those having skill in the art.

5.3 Use of the Neuregulin Peptides

The neuregulin peptides according to the invention can be used according to the judgment of those of skill in the art. Exemplary uses are described in for example, in U.S. Pat. Nos. 7,226,907, 5,367,060, WO 94/026298, WO 03/099300, the contents of each of which are incorporated by reference in its entirety.

The neuregulin peptide are useful in treating a wide range of diseases or disorders. Exemplary diseases or disorders include cardiovascular diseases such as heart failure, viral myocarditis or dilated (congestive) cardiomyopathy (DCM), cardiac toxicity, or myocardial infarction.

In some embodiments, the present invention provides a method for treating heart failure in a subject in need thereof comprising administering to the subject an effective amount of the neuregulin peptides of the invention.

The neuregulin peptides may be administered to a subject in the form of a pharmaceutical composition.

The neuregulin peptides can be administered by any route according to the judgment of those of skill in the art, including but not limited to orally, intravenously, intragastrically, intraduodenally, intraperitoneally or intracerebroventricularly.

In a preferred embodiment, a composition for administration is a pharmaceutical composition. Pharmaceutical compositions can comprise a prophylactically or therapeutically effective amount of one or more prophylactic or therapeutic agents (e.g., a co-complex comprising neuregulin, or other prophylactic or therapeutic agent), and a typically one or more pharmaceutically acceptable carriers or excipients. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E.W. Martin.

Typical pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

The pharmaceutical compositions may comprise excipients that are well known in the art and are listed, for example, in the U.S. Pharmocopia (USP) SP (XXI)/NF (XVI). In general, lactose-free compositions comprise an active ingredient, a binder/filler, and a lubricant in pharmaceutically compatible and pharmaceutically acceptable amounts. Exemplary lactose-free dosage forms comprise an active ingredient, microcrystalline cellulose, pre-gelatinized starch, and magnesium stearate.

The invention further encompasses administration of pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent preferably in purified form, together with a suitable amount of carrier so as to provide the form for proper administration to the patient. The formulation should suit the mode of administration. In a preferred embodiment, the pharmaceutical compositions or single unit dosage forms are sterile and in suitable form for administration to a subject, preferably an animal subject, more preferably a mammalian subject, and most preferably a human subject.

A pharmaceutical composition comprising neuregulin is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the neuregulin peptides will typically vary depending on their use. For example, a dosage form used in the acute treatment of a disorder may contain larger amounts of one or more of neuregulin it comprises than a dosage form used in the chronic treatment of the same disease. Also, the therapeutically effective dosage form may vary among different types of cancer. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

The neuregulin peptides can be administered by any route according to the judgment of those of skill in the art, including but not limited to orally, intravenously, intragastrically, intraduodenally, intraperitoneally or intracerebroventricularly.

5.3.1 Dosage and Routes of Administration

The amount of the neuregulin peptides used in the present invention will vary with the nature and severity of the disease or condition, and the route by which the active ingredient is administered. The frequency and dosage will also vary according to factors specific for each patient depending on the specific therapy (e.g., therapeutic or prophylactic agents) administered, the severity of the disorder, disease, or condition, the route of administration, as well as age, body, weight, response, and the past medical history of the patient. Effective doses may be extrapolated from dose-response curves derived from in vitro or animal model test systems.

Exemplary doses of the neuregulin peptides include milligram or microgram amounts of neuregulin per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). For example, the dosage administered to a patient is typically 0.001 mg/kg to 15 mg/kg of the patient's body weight, based on weight of the active peptide. Preferably, the dosage administered to a patient is between 0.001 mg/kg and 15 mg/kg, 0.005 mg/kg and 10 mg/kg, 0.01 mg/kg and 5 mg/kg, 0.001 mg/kg and 4 mg/kg, 0.005 mg/kg and 3 mg/kg, 0.01 mg/kg and 2 mg/kg, 0.001 mg/kg and 1 mg/kg, 0.005 mg/kg and 0.5 mg/kg, 0.010 mg/kg and 0.2 mg/kg, 0.005 mg/kg and 0.050 mg/kg of the patient's body weight.

Exemplary doses of the neuregulin peptides also include unit (U) or unit amounts of neuregulin per kilogram of subject or sample weight (e.g., about 1 U per kilogram to about 5000 U per kilogram, about 10 U micrograms per kilogram to about 1000 per kilogram, or about 100 U per kilogram to about 500 U per kilogram). For the neuregulin peptides of the invention, the dosage administered to a patient is typically 10 U/kg to 1000 U/kg of the patient's body weight, based on weight of the active peptide. Preferably, the dosage administered to a patient is between 1 U/kg and 10,000U/kg, 1 U/kg and 5000 U/kg, 10 U/kg and 5000 U/kg, 10 U/kg and 1000 U/kg, 50 U/kg and 2000 U/kg, 50 U/kg and 1000/kg, 50 U/kg and 500 U/kg, 100 U/kg and 1000 U/kg, 100 U/kg and 500 U/kg, 100 U/kg and 200 U/kg, of the patient's body weight.

In general, the recommended daily dose range of the neuregulin peptides in the methods of the invention for the conditions described herein lie within the range of from about 0.001 mg to about 1000 mg per day. Specifically, a total daily dose range should be between 0.001 mg per day and 15 mg per day, 0.005 mg per day and 10 mg per day, 0.01 mg per day and 5 mg per day, 0.001 mg per day and 4 mg per day, 0.005 mg per day and 3 mg per day, 0.01 mg per day and 2 mg per day, 0.001 mg per day and 1 mg per day, 0.005 mg per day and 0.5 mg per day, 0.010 mg per day and 0.2 mg per day. In managing the patient, the therapy can be initiated at a lower dose, perhaps about 0.1 µg to about 1 µg, and increased if necessary up to about 20 µg to about 1000 µg per day as either a single dose or divided doses, depending on the patient's global response. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response. In certain embodiments, neuregulin is administered in an amount of about 1 U/day to about 10,000 U/day. In some embodiments, it is administered in an amount of about 1 U/day to about 5000 U/day. In some embodiments, it is administered in an amount of about 10 U/day to about 2000 U/day. In some embodiments, it is administered in an amount of about 10 U/day to about 1000 U/day. In some embodiments, it is administered in an amount of about 100 U/day to about 200 U/day.

The neuregulin peptides can also be administered in a dosing schedule or "therapeutic cycle." Daily dosage of neuregulin in the therapeutic cycle is described in detail above. The therapeutic cycle can last 2 days, 5 days, 7 days, 10 days, two weeks, three weeks, four weeks, five weeks, or six weeks.

In certain embodiments, neuregulin is administered daily for each day of the therapeutic cycle. In certain embodiments, neuregulin is administered consecutively for three, four, five, six, seven, eight, nine, ten, eleven or twelve days in a therapeutic cycle. In certain embodiments, in a therapeutic cycle neuregulin is administered on day 1 of the cycle and the cycle concludes with one or more days of no neuregulin administration In some embodiments, neuregulin is administered daily for 3, 5, 7, or 10 days followed by a resting period in a therapeutic cycle.

6. EXAMPLES

6.1 Example 1 Chemically Synthesis of Neuregulin Peptides

Five neuregulin peptides NRG53 (SEQ ID NO: 3), NRG55 (SEQ ID NO: 4), NRG57 (SEQ ID NO: 5), NRG59 (SEQ ID NO: 6), NRG61 (SEQ ID NO: 1) were synthesized by GL Biochem (Shanghai) Ltd.

NRG61 comprises the amino acid sequence of Ser His Leu Val Lys Cys Ala Glu Lys Glu Lys Thr Phe Cys Val Asn Gly Gly Glu Cys Phe Met Val Lys Asp Leu Ser Asn Pro Ser Arg Tyr Leu Cys Lys Cys Pro Asn Glu Phe Thr Gly Asp Arg Cys Gln Asn Tyr Val Met Ala Ser Phe Tyr Lys Ala Glu Glu Leu Tyr Gln (SEQ ID NO:1), which corresponds to amino acids 177-237 of human NRG-1.

The human nucleic acid sequence encoding the fragment is:
agccatcttg taaaatgtgc ggagaaggag aaaactttct gtgtgaatgg aggggagtgc ttcatggtga aagacctttc aaaccccctcg agatacttgt gcaagtgccc aaatgagttt actggtgatc gctgccaaaa ctacgtaatg gcgagcttct acaaggcgga ggagctgtac cag (SEQ ID NO:2).

Neuregulin peptide EGF53 has the amino acid sequence:
Ser His Leu Val Lys Cys Ala Glu Lys Glu Lys Thr Phe Cys Val Asn Gly Gly Glu Cys Phe Met Val Lys Asp Leu Ser Asn Pro Ser Arg Tyr Leu Cys Lys Cys Pro Asn Glu Phe Thr Gly Asp Arg Cys Gln Asn Tyr Val Met Ala Ser Phe (SEQ ID NO:3).

The human nucleic acid sequence encoding the fragment is:
agccatcttg taaaatgtgc ggagaaggag aaaactttct gtgtgaatgg aggggagtgc ttcatggtga aagacctttc aaaccccctcg agatacttgt gcaagtgccc aaatgagttt actggtgatc gctgccaaaa ctacgtaatg gcgagcttc (SEQ ID NO:4).

Neuregulin peptide NRG55 comprises the amino acid sequence:
Ser His Leu Val Lys Cys Ala Glu Lys Glu Lys Thr Phe Cys Val Asn Gly Gly Glu Cys Phe Met Val Lys Asp Leu Ser Asn Pro Ser Arg Tyr Leu Cys Lys Cys Pro Asn Glu Phe Thr Gly Asp Arg Cys Gln Asn Tyr Val Met Ala Ser Phe Tyr Lys (SEQ ID NO:5).

The human nucleic acid sequence encoding the fragment is:
agccatcttg taaaatgtgc ggagaaggag aaaactttct gtgtgaatgg aggggagtgc ttcatggtga aagacctttc aaaccccctcg agatacttgt gcaagtgccc aaatgagttt actggtgatc gctgccaaaa ctacgtaatg gcgagcttct acaag (SEQ ID NO:6).

Neuregulin peptide NRG57 comprises the amino acid sequence:
Ser His Leu Val Lys Cys Ala Glu Lys Glu Lys Thr Phe Cys Val Asn Gly Gly Glu Cys Phe Met Val Lys Asp Leu Ser Asn Pro Ser Arg Tyr Leu Cys Lys Cys Pro Asn Glu Phe Thr Gly Asp Arg Cys Gln Asn Tyr Val Met Ala Ser Phe Tyr Lys Ala Glu (SEQ ID NO:7).

The human nucleic acid sequence encoding the fragment is:
agccatcttg taaaatgtgc ggagaaggag aaaactttct gtgtgaatgg aggggagtgc ttcatggtga aagacctttc aaaccccctcg agatacttgt gcaagtgccc aaatgagttt actggtgatc gctgccaaaa ctacgtaatg gcgagcttct acaaggcgga g (SEQ ID NO:8).

Neuregulin peptide NRG59 comprises the amino acid sequence:
Ser His Leu Val Lys Cys Ala Glu Lys Glu Lys Thr Phe Cys Val Asn Gly Gly Glu Cys Phe Met Val Lys Asp Leu Ser Asn Pro Ser Arg Tyr Leu Cys Lys Cys Pro Asn Glu Phe Thr Gly Asp Arg Cys Gln Asn Tyr Val Met Ala Ser Phe Tyr Lys Ala Glu Glu Leu (SEQ ID NO:9).

The human nucleic acid sequence encoding the fragment is:
agccatcttg taaaatgtgc ggagaaggag aaaactttct gtgtgaatgg aggggagtgc ttcatggtga aagacctttc aaaccccctcg agatacttgt gcaagtgccc aaatgagttt actggtgatc gctgccaaaa ctacgtaatg gcgagcttct acaaggcgga ggagctg (SEQ ID NO:10).

Each peptide was separately dissolved in buffer 1 (0.1M $Na_2HPO_4$, 0.1 M citric acid, 6M Urea, 1 mM $EDTA-Na_2$, 5 mM DTT, pH 8.0) at 1 mg/ml, the peptide solution was then left at room temperature for 1 hour. 1ml sample solution was mixed with 9 ml buffer 2 (0.01M $Na_2HPO_4$, 0.01M citric acid, 1 mM $EDTA-Na_2$, 0.5 mM GSSG, 0.5 mM GSH, pH 8.0) so the final protein concentration was 0.1 mg/ml. The solution was then stirred at room temperature for 90 minutes before left at 4° C. for 16 hours. The sample was then loaded onto a G25 column and collected in buffer 3 (20 mM $Na_2HPO_4$, 20 mM $NaH_2PO_4$, pH 6.0).

6.2 Example 2 Receptor Bindings of Chemically Synthesized Five Neuregulin Peptides MCF-7 cells was harvested, counted, pelleted and resuspended into DMEM (with 10% serum and 9 μg/ml insulin) at $5 \times 10^4$ cells/ml. 100 μl cell suspension was added to each well of 96 well plate and the plate was incubated at 37° C. overnight. The cells were then washed 3 times with PBS and grew in serum free DMEM for another 24 hours.

ErbB2 antibody H4 (Zensun, anti-ErbB2 monoclonal antibody) was diluted to 6 μg/ml by coating buffer (50 mM $Na_2CO_3$-$NaHCO_3$, pH9.6), and added to 96 well plate 50 μl/well. The plate was left at 4° C. overnight to coat with antibody.

DMEM was sucked away from the starved MCF-7 cells, and 100 μl serial dilutions of NRG, NRG53, NRG55, NRG57, NRG59 or NRG61 in DMEM were added to each well separately. DMEM was added to two wells as blank. The plate was incubated at 37° C. for 20 min. The cells were washed once with PBS before adding 100 μl/ well lysis buffer (50 mM Hepes, pH 8.0, 150 mM NaCl, 2 mM sodium orthovanadate, 0.01% thimerosal, 1% Triton X-100 and one protease inhibitor cocktail tablet per 25 ml solution) and lysing at 4° C. for 30 min. The plate was then shaken gently to completely lyse and remove cells from the plate and centrifuged at 15000 rpm for 15 min.

The plate with coating antibody was washed five times with washing buffer (10 mM PBS, pH7.4, 0.05% Tween 20) before adding 200 μl/well of 5% nonfat milk in washing buffer. The plate was incubated at 37° C. for 2 hours before washed again 3 times with washing buffer.

A 90 μl solution of lysed cells was drawn from each well in culture plate and transferred to corresponding well in coated plate. Following incubation at 37° C. for 1 hour, the coated plate with cell lysis was washed again 5 times with washing buffer and treated with 100 μl suitable concentration of horseradish peroxidase (HRP) conjugated anti-phosphotyrosine monoclonal antibody (Santa Cruz Biotechnology) at 37° C. for 1 hour. After the plate was washed again 5 times with washing buffer, 100 μl freshly prepared HRP substrate solution [50 mM citric acid, 100 mM $Na_2PO_4$, pH 5.0, 0.2 mg/ml 3,3',5,5'-tetramethylbenzidine (TMB), 0.003% $H_2O_2$] was added to each well before the plate was incubated at 37° C. for 10 min. Finally 50 μl of 2N $H_2SO_4$ was added to each well to destroy HRP activity. The OD value at 450 nm for each well was read on a microplate reader (BIO-RAD Model 550), and EC50 was the concentration of neuregulin peptides which achieved 50% of maximum OD value. The lower the $EC_{50}$, the higher the receptor binding affinity of the neuregulin peptides.

The $EC_{50}$ of NRG (full length wild type neuregulin β2 peptide) NRG53, NRG55, NRG57, NRG59 and NRG61 was shown in Table 1.

TABLE 1

| $EC_{50}$ of NRG, NRG53, NRG55, NRG57, NRG59 and NRG61 | |
| --- | --- |
| sample | EC50 (μg/ml) |
| NRG | 0.2772 |
| NRG53 | 0.814 |

TABLE 1-continued

| $EC_{50}$ of NRG, NRG53, NRG55, NRG57, NRG59 and NRG61 | |
| --- | --- |
| sample | EC50 (μg/ml) |
| NRG55 | 0.0492 |
| NRG57 | 0.9783 |
| NRG59 | 0.4605 |
| NRG61 | 1.439 |

As shown in table 1, $EC_{50}$ of NRG55 is much lower than that of NRG.

6.3 Example 3 Effect of Chemically Synthesized Neuregulin Peptides on the Phosphorylation of AKT in Cardiomyocytes To study the effect of synthesized peptides on ErbB2 and ErbB4 signaling in cardiomyocytes, cardiac cells extracted from left ventricles of neonatal rats were used.

Cardiac cells were grown in media with serum for 2 days. After the cells reached about 80% confluence, the media was changed to serum free media. After another 24 hours, different amounts of synthesized neuregulin peptides or neuregulin were added into separate wells containing the cells for 20 minutes. The media was then aspirated and gel loading buffer was added to lyse the cells. The sample was then harvested and loaded into a separate well of gel for electrophoresis and western blot analysis.

FIG. 1 shows the effect of the neuregulin peptides at different concentration on AKT phosphorylation. As shown in FIG. 1, NRG57 and NRG59 almost have the same effect as NRG, NRG55 has much stronger effect than NRG. The result suggests that NRG55 can be a more effective peptide for treating cardiovascular disease.

The scope of the invention is not limited by the description of the examples. Modifications and alterations of the present invention will be apparent to those skilled in the art without departing from the scope and spirit of the present invention. Therefore, it will be appreciated that the scope of this invention is to be defined by the appended claims, rather than by the specific examples which have been presented by way of example.

What is claimed is:

1. A method for treating heart failure in a subject in need thereof comprising administering intravenously or subcutaneously to the subject and effective amount of neuregulin peptide consisting of the amino acid sequence of SEQ ID NO:3, SEQ ID NO:5, SEQ ID NO:7 or SEQ ID NO:9.

2. The method of claim 1, wherein the neuregulin peptide consists of the amino acid sequence of SEQ ID NO:3.

3. The method of claim 2, wherein the neuregulin peptide is administered intravenously.

4. The method of claim 2, wherein the neuregulin peptide is administered subcutaneously.

5. The method of claim 1, wherein the neuregulin peptide consists of the amino acid sequence of SEQ ID NO:5 and is administered intravenously.

6. The method of claim 1, wherein the neuregulin peptide consists of the amino acid sequence of SEQ ID NO:5 and is administered subcutaneously.

7. The method of claim 1, wherein the neuregulin peptide consists of the amino acid sequence of SEQ ID NO:7.

8. The method of claim 7, wherein the neuregulin peptide is administered intravenously.

9. The method of claim 7, wherein the neuregulin peptide is administered subcutaneously.

10. The method of claim 1, wherein the neuregulin peptide consists of the amino acid sequence of SEQ ID NO:9.

11. The method of claim 10, wherein the neuregulin peptide is administered intravenously.

12. The method of claim 10, wherein the neuregulin peptide is administered subcutaneously.

13. The method of any one of claim 1, 2, 3, 4, 5-7, 8-10, 11 or 12, wherein the subject is human.

* * * * *

SEQUENCE LISTING

```
<160> NUMBER OF SEQ ID NOS: 11

<210> SEQ ID NO 1
<211> LENGTH: 61
<212> TYPE: PRT
<213> ORGANISM: Homo sapiens

<400> SEQUENCE: 1

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln
    50                  55                  60

<210> SEQ ID NO 2
<211> LENGTH: 183
<212> TYPE: DNA
<213> ORGANISM: Homo sapiens
```

<400> SEQUENCE: 2

```
agccatcttg taaaatgtgc ggagaaggag aaaactttct gtgtgaatgg aggggagtgc    60
ttcatggtga agacctttc aaaccccctcg agatacttgt gcaagtgccc aaatgagttt   120
```

```
agccatcttg taaaatgtgc ggagaaggag aaaactttct gtgtgaatgg aggggagtgc    60
ttcatggtga agacctttc aaaccccctcg agatacttgt gcaagtgccc aaatgagttt   120
actggtgatc gctgccaaaa ctacgtaatg gcgagcttct acaaggcgga ggagctgtac   180
cag                                                                 183
```

<210> SEQ ID NO 3
<211> LENGTH: 53
<212> TYPE: PRT
<213> ORGANISM: Homo sapiens

<400> SEQUENCE: 3

```
Ser His Leu Val Lys Cys Ala Glu Lys Glu Lys Thr Phe Cys Val Asn
  1               5                  10                  15

Gly Gly Glu Cys Phe Met Val Lys Asp Leu Ser Asn Pro Ser Arg Tyr
             20                  25                  30

Leu Cys Lys Cys Pro Asn Glu Phe Thr Gly Asp Arg Cys Gln Asn Tyr
         35                  40                  45

Val Met Ala Ser Phe
     50
```

<210> SEQ ID NO 4
<211> LENGTH: 159
<212> TYPE: DNA
<213> ORGANISM: Homo sapiens

<400> SEQUENCE: 4

```
agccatcttg taaaatgtgc ggagaaggag aaaactttct gtgtgaatgg aggggagtgc    60
ttcatggtga agacctttc aaaccccctcg agatacttgt gcaagtgccc aaatgagttt   120
actggtgatc gctgccaaaa ctacgtaatg gcgagcttc                          159
```

<210> SEQ ID NO 5
<211> LENGTH: 55
<212> TYPE: PRT
<213> ORGANISM: Homo sapiens

<400> SEQUENCE: 5

```
Ser His Leu Val Lys Cys Ala Glu Lys Glu Lys Thr Phe Cys Val Asn
  1               5                  10                  15

Gly Gly Glu Cys Phe Met Val Lys Asp Leu Ser Asn Pro Ser Arg Tyr
             20                  25                  30

Leu Cys Lys Cys Pro Asn Glu Phe Thr Gly Asp Arg Cys Gln Asn Tyr
         35                  40                  45

Val Met Ala Ser Phe Tyr Lys
     50                  55
```

<210> SEQ ID NO 6
<211> LENGTH: 165
<212> TYPE: DNA
<213> ORGANISM: Homo sapiens

<400> SEQUENCE: 6

```
agccatcttg taaaatgtgc ggagaaggag aaaactttct gtgtgaatgg aggggagtgc    60
ttcatggtga aagacctttc aaaccccctcg agatacttgt gcaagtgccc aaatgagttt   120
actggtgatc gctgccaaaa ctacgtaatg gcgagcttct acaag                    165
```

```
<210> SEQ ID NO 7
<211> LENGTH: 57
<212> TYPE: PRT
<213> ORGANISM: Homo sapiens

<400> SEQUENCE: 7
```

```
Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu
    50                  55
```

```
<210> SEQ ID NO 8
<211> LENGTH: 171
<212> TYPE: DNA
<213> ORGANISM: Homo sapiens

<400> SEQUENCE: 8
```

```
agccatcttg taaaatgtgc ggagaaggag aaaactttct gtgtgaatgg aggggagtgc    60
ttcatggtga aagacctttc aaaccccctcg agatacttgt gcaagtgccc aaatgagttt   120
actggtgatc gctgccaaaa ctacgtaatg gcgagcttct acaaggcgga g             171
```

```
<210> SEQ ID NO 9
<211> LENGTH: 59
<212> TYPE: PRT
<213> ORGANISM: Homo sapiens

<400> SEQUENCE: 9
```

```
Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu
    50                  55
```

```
<210> SEQ ID NO 10
<211> LENGTH: 177
<212> TYPE: DNA
<213> ORGANISM: Homo sapiens

<400> SEQUENCE: 10
```

```
agccatcttg taaaatgtgc ggagaaggag aaaactttct gtgtgaatgg aggggagtgc    60
ttcatggtga aagacctttc aaaccccctcg agatacttgt gcaagtgccc aaatgagttt   120
actggtgatc gctgccaaaa ctacgtaatg gcgagcttct acaaggcgga ggagctg       177
```

```
<210> SEQ ID NO 11
<211> LENGTH: 23
<212> TYPE: PRT
<213> ORGANISM: Homo sapiens
```

```
<400> SEQUENCE: 11

Ala Glu Lys Glu Lys Thr Phe Cys Val Asn Gly Gly Glu Cys Phe Met
 1               5                  10                  15

Val Lys Asp Leu Ser Asn Pro
            20
```